United States Patent [19]
Zoller et al.

[11] Patent Number: 5,681,838
[45] Date of Patent: Oct. 28, 1997

[54] SUBSTITUTED AMINO COMPOUNDS, THEIR PREPARATION AND THEIR USE AS INHIBITORS OF THROMBOCYTE-AGGREGATION

[75] Inventors: Gerhard Zoller, Schöneck; Bernd Jablonka, Bad Soden; Melitta Just, Langen; Otmar Klingler, Rodgau; Gerhard Breipohl, Frankfurt am Main; Jochen Knolle, Kriftel; Wolfgang König, Stallwang, all of Germany

[73] Assignee: Hoechst Aktiengesellschaft, Frankfurt am Main, Germany

[21] Appl. No.: 491,952

[22] PCT Filed: Jan. 7, 1994

[86] PCT No.: PCT/EP91/00029

§ 371 Date: Jul. 18, 1995

§ 102(e) Date: Jul. 18, 1995

[87] PCT Pub. No.: WO94/17034

PCT Pub. Date: Aug. 4, 1994

[30] Foreign Application Priority Data

Jan. 23, 1993 [DE] Germany .................... 43 01 747.9

[51] Int. Cl.⁶ .................... A61K 31/47; A61K 31/415; A61K 31/205

[52] U.S. Cl. .................... 514/307; 514/398; 514/555; 546/152; 548/318.5; 562/439; 562/440; 562/443

[58] Field of Search .................... 562/439, 440, 562/443; 514/307, 398, 555; 546/152; 548/318.5

[56] References Cited

PUBLICATIONS

Int. J. of Peptide and Protein Research, 23(2), 203–211 1984.

*Primary Examiner*—Joseph Conrad

[57] ABSTRACT

The present invention relates to novel substituted amino compounds of the formula I:

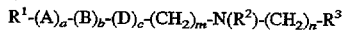

$$R^1\text{-}(A)_a\text{-}(B)_b\text{-}(D)_c\text{-}(CH_2)_m\text{-}N(R^2)\text{-}(CH_2)_n\text{-}R^3$$

as defined in the present application, and to a process for preparing such compounds. The invention also includes pharmaceutical compositions containing the present compounds, and the preparation of such compositions. The invention also relates to the use of the present compounds as inhibitors of blood-platelet aggregation, formation of metastases by carcinoma cells, and the binding of osteoclasts to bone surfaces, in the treatment of hosts in need thereof.

7 Claims, No Drawings

SUBSTITUTED AMINO COMPOUNDS, THEIR PREPARATION AND THEIR USE AS INHIBITORS OF THROMBOCYTE-AGGREGATION

The present invention relates to substituted amino compounds, their preparation and their use as inhibitors of blood platelet aggregation.

EP-A 449 079 describes hydantoin derivatives which exhibit thrombocyte-aggregation-inhibiting effects. Further research has shown that the compounds of the present invention are also strong inhibitors of blood platelet aggregation.

The present invention relates to compounds of the general formula I

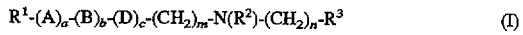

$$R^1\text{-}(A)_a\text{-}(B)_b\text{-}(D)_c\text{-}(CH_2)_m\text{-}N(R^2)\text{-}(CH_2)_n\text{-}R^3 \qquad (I)$$

in which
A denotes a divalent radical from the group comprising ($C_1$–$C_6$)-alkylene, ($C_5$–$C_6$)-cycloalkylene, phenylene, phenylene-($C_1$–$C_6$)-alkyl, phenylene-($C_2$–$C_6$)-alkenyl, phenylene-($C_1$–$C_6$)-alkylidene and hetylene, where Het represents a 5- or 6-membered ring which can contain up to 3 hetero atoms from the group comprising nitrogen, oxygen and sulphur, and which can be substituted once or twice by ($C_1$–$C_6$)-alkyl or doubly bonded oxygen or sulphur; B denotes a divalent radical from the group comprising ($C_1$–$C_6$)-alkylene, ($C_2$–$C_6$)-alkenylene, phenylene, carbonyl and hetylene, where Het is defined as indicated above; D denotes a divalent radical from the group comprising nitrogen, oxygen, sulphur, carbonyl, carbonyloxy, oxycarbonyl, carbonylimino, iminocarbonyl, iminocarbonylimino and iminothiocarbonylimino, or a natural or unnatural amino acid, imino acid or azaamino acid which is linked in a peptide-like manner via the C- and N-termini,
$R^1$ denotes —($CH_2$)$_o$-NH-X or —($CH_2$)$_p$-C(=NH)-NH-$X^1$, where o and p represent an integer from 0 to 3;
$X^1$ denotes hydrogen, ($C_1$–$C_6$)-alkyl, ($C_1$–$C_6$)-alkoxy, ($C_1$–$C_6$)-alkylcarbonyl, ($C_1$–$C_6$)-alkoxycarbonyl, ($C_6$–$C_{14}$)-aryloxycarbonyl, ($C_6$–$C_{14}$)-arylcarbonyl, ($C_1$–$C_{18}$)-alkylcarbonyloxy-($C_1$–$C_6$)-alkoxycarbonyl, ($C_6$–$C_{14}$)-aryl-($C_1$–$C_6$)-alkoxycarbonyl, cyano, hydroxyl or amino;
X has one of the meanings of $X^1$ or denotes —C(=N-R")-NH-R', where R' and R" are, independently of each other, defined as $X^1$;
$R^2$ denotes hydrogen, ($C_1$–$C_8$)-alkyl, —$COR^4$, —$COOR^4$, —CO-N($CH_3$)-$R^4$, —CO-NH-$R^4$ or —CS-NH-$R^4$;
$R^3$ denotes —$COR^9$, —$SO_2OH$, —$SO_2NH$-$R^{10}$ or tetrazolyl;
$R^4$ denotes hydrogen, or denotes ($C_1$–$C_{28}$)-alkyl which is optionally substituted once or more than once by identical or different radicals from the group comprising hydroxyl, hydroxycarbonyl, aminocarbonyl, mono- or di-($C_1$–$C_{18}$)-alkylaminocarbonyl, amino-($C_2$–$C_{14}$)-alkylaminocarbonyl, amino-($C_1$–$C_3$)alkylphenyl-($C_1$–$C_3$)alkylaminocarbonyl, ($C_1$–$C_{18}$)-alkylcarbonylamino-($C_1$–$C_3$)-alkylphenyl-($C_1$–$C_3$)alkylaminocarbonyl, ($C_1$–$C_{18}$)-alkylcarbonylamino-($C_2$–$C_{14}$)-alkylaminocarbonyl, phenyl-($C_1$–$C_8$)-alkoxycarbonyl, amino, mercapto, ($C_1$–$C_{18}$)-alkoxy, ($C_1$–$C_{18}$)-alkoxycarbonyl, ($C_3$–$C_8$)-cycloalkyl, halogen, nitro, trifluoromethyl or a radical $R^5$;
$R^5$ denotes ($C_6$–$C_{14}$)-aryl, ($C_6$–$C_{14}$)-aryl-($C_1$–$C_8$)-alkyl, a monocyclic or bicyclic 5- to 12-membered heterocyclic ring, which can be aromatic, partially hydrogenated or completely hydrogenated, and which can contain, as hetero element, one, two or three identical or different nitrogen, oxygen or sulphur atoms, or denotes a radical $R^6$, where the aryl radical and, independently thereof, the heterocycle radical can optionally be substituted once or more than once by identical or different radicals from the group comprising ($C_1$–$C_{18}$)-alkyl, ($C_1$–$C_{18}$)-alkoxy, halogen, nitro or trifluoromethyl;
$R^6$ denotes —$NR^7R^8$, —$OR^7$, —$SR^7$, an amino acid side chain, a natural or unnatural amino acid residue, imino acid residue, optionally N-($C_1$–$C_8$)-alkylated or ($C_6$–$C_{14}$)-aryl-($C_1$–$C_8$)-alkylated azaamino acid residue or dipeptide residue, in which the peptide bond can be reduced to NH-$CH_2$, as well as esters and amides thereof, where free functional groups can optionally be substituted by hydrogen or hydroxymethyl or can be protected by protective groups which are customary in peptide chemistry, or denotes a radical —$COR^{6'}$, in which $R^{6'}$ is defined as $R^6$;
$R^7$ denotes hydrogen, ($C_2$–$C_{18}$)-alkyl, ($C_6$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_6$–$C_{14}$)-arylcarbonyl, ($C_6$–$C_{14}$)-aryl-($C_1$–$C_8$)-alkylcarbonyl, ($C_6$–$C_{14}$)-aryl-($C_1$–$C_{18}$)-alkoxycarbonyl, where the alkyl groups can optionally be substituted by an amino group, a natural or unnatural amino acid residue, imino acid residue, optionally N-($C_1$–$C_6$)-alkylated or ($C_6$–$C_{14}$)-aryl-($C_1$–$C_8$)-alkylated azaamino acid residue or a dipeptide residue, in which the peptide bond can be reduced to NH-$CH_2$;
$R^8$ denotes hydrogen, ($C_1$–$C_{18}$)-alkyl, ($C_6$–$C_{14}$)-aryl or ($C_6$–$C_{14}$)-aryl-($C_1$–$C_8$)-alkyl;
$R^9$ denotes hydroxyl, ($C_1$–$C_{18}$)-alkoxy, ($C_6$–$C_{14}$)-aryl-($C_1$–$C_8$)-alkoxy, amino, or mono- or di-($C_1$–$C_{18}$)-alkylamino;
$R^{10}$ denotes hydrogen, ($C_1$–$C_{18}$)-alkylaminocarbonyl or ($C_3$–$C_8$)-cycloalkylaminocarbonyl;
a, b and c represent 0 or 1, but cannot all simultaneously be 0; and
m and n, independently of each other, represent an integer from 1 to 6,
as well as physiologically tolerated salts thereof.

Alkyl radicals may be straight-chain or branched. Preferred alkyl radicals are methyl, ethyl, n-propyl, i-propyl, n-butyl, i-butyl, sec-butyl and tert-butyl. The same applies in a corresponding manner for radicals such as alkylene, alkoxy, alkoxycarbonyl or aralkyl.

Alkenylene radicals can also be straight-chain or branched. Preferred alkenylene radicals are vinylene and propenylene.

Cycloalkyl radicals are, in particular, cyclopropyl, cyclobutyl, cyclopentyl, cyclohexyl, cycloheptyl and cyclooctyl, which, however, may also be substituted by, for example, ($C_1$–$C_4$)-alkyl. Examples of substituted cycloalkyl radicals are 4-methylcyclohexyl and 2,3-dimethylcyclopentyl. The same applies in an analogous manner for cycloalkylene radicals.

($C_6$–$C_{14}$)-Aryl groups are, for example, phenyl, naphthyl, biphenylyl or fluorenyl, where phenyl and naphthyl are preferred. The same applies in a corresponding manner for radicals such as aralkyl or arylcarbonyl. Aralkyl radicals are, in particular, benzyl as well as 1- and 2-naphthylmethyl, which may also be substituted. Substituted aralkyl radicals are, for example, halobenzyl or ($C_1$–$C_4$)-alkoxybenzyl.

If phenyl is substituted twice, the substituents can be located in the 1,2, 1,3 or 1,4 positions with regard to each other. The 1,3 and the 1,4 positions are preferred.

Phenylene-($C_1$–$C_6$)-alkyl is, in particular, phenylenemethyl and phenyleneethyl. Phenylene-($C_2$–$C_6$)-alkenyl is, in particular, phenyleneethenyl and phenylenepropenyl. A phenylene-($C_1$–$C_6$)-alkylidene radical is, for example, phenylenemethylene.

Examples of Het are, in particular, pyrrolidone, imidazolidine, thiazolidine and oxazolidine, but also piperidine, piperazine, morpholine and thiomorpholine.

Monocyclic or bicyclic 5- to 12-membered heterocyclic rings within the meaning of the above definitions are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxylinyl, quinazolinyl, cinnolinyl, or a benzo-fused, cyclopenta-fused, cyclohexa-fused or cyclohepta-fused derivative of these radicals.

These heterocycles can be substituted on a nitrogen atom by oxides, $(C_1-C_7)$-alkyl, e.g. methyl or ethyl, phenyl or phenyl-$(C_1-C_4)$-alkyl, e.g. benzyl, and/or on one or more carbon atoms by $(C_1-C_4)$-alkyl, halogen, hydroxyl, $(C_1-C_4)$-alkoxy, e.g. methoxy, phenyl-$(C_1-C_4)$-alkoxy, e.g. benzyloxy or oxo, and be partially or completely saturated.

Radicals of this type are, for example, 2- or 3-pyrrolyl, phenyl-pyrrolyl, e.g. 4- or 5-phenyl-2-pyrrolyl, 2-furyl, 2-thienyl, 4-imidazolyl, methylimidazolyl, e.g. 1-methyl-2-, 4- or 5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxylinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, e.g. 2-, 3- or 4-N-methylpyrrolidinyl, piperazinyl, morpholinyl, thiomorpholinyl, tetrahydrothienyl or benzodioxolanyl.

Halogen represents fluorine, chlorine, bromine or iodine, in particular fluorine or chlorine.

Natural and unnatural amino acids can, if chiral, be present in the D or L form. α-Amino acids are preferred. Those which may be mentioned by way of example are (cf. Houben-Weyl, Methoden der organischen Chemie [Methods of Organic Chemistry], Volume XV/1 and 2, Stuttgart, 1974): Aad, Abu, βAbu, ABz, 2ABz, εAca, Ach, Acp, Adpd, Ahb, Aib, βAib, Ala, βAla, βAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, bile, bleu, hLys, hMet, hPhe, hPro, hSer, hThr, hTrp, hTyr, Hyl, Hyp, 3Hyp, Ile, Ise, Ira, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl)aminoacetic acid.

Amino acid side chains are understood to mean side chains of natural or unnatural amino acids. Azaamino acids are natural or unnatural amino acids in which the central structural component —CHR— or —CH$_2$— is replaced by —NR— or —NH—, respectively.

Residues of heterocycles from the following group are particularly suitable for use as the residue of an imino acid: Pyrrolidine-2-carboxylic acid; piperidine-2-carboxylic acid, tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo-[2.2.1]heptane-3-carboxylic acid; 2-azabicyclo[3.1.0]-hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid and hydroxyproline-2-carboxylic acid; which can all be optionally substituted (see formulae below):

The heterocycles on which the abovementioned residues are based are known, for example, from U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

As their structural components, dipeptides can contain natural or unnatural amino acids, imino acids and azaamino acids. Furthermore, the natural or unnatural amino acids, imino acids, azaamino acids and dipeptides can also be present as esters or amides, such as, for example, methyl esters, ethyl amide, semicarbazide or ω-amino-$(C_4-C_8)$-alkyl amide.

Functional groups of the amino acids, imino acids and dipeptides may be present in the protected form. Suitable protective groups, such as, for example, urethane protective groups, carboxyl protective groups and side-chain protective groups are described in Hubbuch, Kontakte [Contacts] (Merck) 1979, No. 3, pages 14 to 23 and in Büllesbach, Kontakte [Contacts] (Merck) 1980, No. 1, pages 23 to 35. Those which may, in particular, be mentioned are: Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Physiologically tolerated salts of the compounds of the general formula I are, in particular, pharmaceutically utilizable or non-toxic salts.

Such salts are formed, for example, from compounds of the general formula I which contain acid groups, e.g. carboxyl, with alkali metals or alkaline earth metals, such as, for example, Na, K, Mg and Ca, as well as with physiologically tolerated organic amines, such as, for example, triethylamine and tris(2-hydroxyethyl)amine.

Compounds of the general formula I which contain basic groups, e.g. an amino group or a guanidino group, form salts with inorganic acids, such as, for example, hydrochloric acid, sulphuric acid or phosphoric acid, and with organic carboxylic or sulphonic acids, such as, for example, acetic acid, citric acid, benzoic acid, maleic acid, fumaric acid, tartaric acid and p-toluenesulphonic acid.

The compounds of the general formula I according to the invention can contain optically active carbon atoms and thus be present in the form of pure enantiomers or in the form of enantiomeric mixtures. Both pure enantiomers and enantiomeric mixtures are the subject of the present invention.

In addition to this, the compounds of the general formula Z according to the invention may contain moveable hydrogen atoms, that is be present in different tautomeric forms. These tautomers are also the subject matter of the present invention.

Preferred compounds of the general formula I are those in which

A denotes a divalent radical from the group comprising methylene, ethylene, trimethylene, tetramethylene, cyclohexylene, phenylene, phenylenemethyl, phenyleneethenyl, phenylenemethylene, 2,5-dioxoimidazolidine-1,4-diyl and 5-oxo-2-thioxoimidazolidine-1,4-diyl;

B denotes a divalent radical from the group comprising methylene, ethylene, trimethylene, tetramethylene, vinylene, phenylene, 2,5-dioxoimidazolidine-1,4-diyl, 5-oxo-2-thioxoimidazolidine-1,4-diyl, 2,5-dioxopyrrolidine-1,4-diyl and 2,4-dioxooxazolidine-3,5-diyl;

D denotes a divalent radical from the group comprising carbonyl, carbonylimino, iminocarbonyl and iminocarbonylimino;

$R^1$ denotes —$CH_2$-NH-X, —C(=NH)-NH-$X^1$ or —NH-C(=$NX^1$)-NH-$X^1$;

X and $X^1$ denote hydrogen, ($C_1$–$C_6$)-alkylcarbonyl, ($C_1$–$C_6$)-alkoxycarbonyl or ($C_1$–$C_8$)-alkylcarbonyloxy-($C_1$–$C_6$)-alkoxycarbonyl;

$R^2$ denotes —$COR^4$, —$COOR^4$, —CO-NH-$R^4$ or —CS-NH-$R^4$;

$R^3$ denotes —COOH or —COO-($C_1$–$C_{18}$)-alkyl;

$R^4$ denotes ($C_1$–$C_6$)-alkyl or ($C_6$–$C_{14}$)-aryl-($C_1$–$C_8$)-alkyl, or, in the case where $R^2$ represents —CO-NH-$R^4$ or —CS-NH-$R^4$, —NH-$R^4$ represents an α-amino acid residue or its ω-amino-($C_2$–$C_8$)-alkyl amide;

a, b and c denote 0 or 1, but cannot all simultaneously be 0; and m represents 2 or 3 and n represents 1.

The valine, lysine, phenylalanine, tryptophan or phenylglycine residue is particularly preferred as the α-amino acid residue representing —NH-$R^4$.

A particularly preferred ω-amino-($C_2$–$C_8$)-alkyl amide is the 4-aminobutyl amide.

The compounds of the general formula I according to the invention can be prepared by fragment condensation of a compound of the general formula II

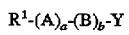  $R^1$-(A)$_a$-(B)$_b$-Y  (II)

with a compound of the general formula III

 Z-(CH$_2$)$_m$-N(R$^2$)-(CH$_2$)$_n$-R$^3$  (III)

in which a, b, m and n, as well as the radicals A, B and $R^1$ to $R^3$ are defined as above, and Y represents hydroxycarbonyl, alkoxycarbonyl or an activated carboxylic acid derivative, such as an acid chloride or an active ester, and Z represents amino or hydroxyl, or in which Y represents amino or hydroxyl, and Z represents hydroxycarbonyl, alkoxycarbonyl or an activated carboxylic acid derivative.

The methods of peptide chemistry which are known per se (see, e.g., Houben Weyl, Methoden der organischen Chemie [Methods of Organic Chemistry], Volumes 15/1 and 15/2, Stuttgart, 1974) are advantageously used for condensing the compounds of the general formula II with those of the general formula III.

For this purpose, it is necessary, as a rule, for amino groups contained in $R^1$ and $R^4$ to be protected by reversible protective groups. The same applies for the carboxyl groups of the compound of the general formula III, which groups preferably are present as ($C_1$–$C_6$)-alkyl, benzyl or tert-butyl esters. Amino group protection is superfluous when the amino groups to be generated are present as nitro or cyano groups and are only formed by hydrogenation following the coupling.

After the coupling, the protective groups which are present are eliminated in a suitable manner. For example, $NO_2$ groups (guanidino protection), benzyloxycarbonyl groups and benzyl esters can be eliminated by hydrogenation. Protective groups of the tert-butyl type are cleaved under acid conditions, while the 9-fluorenylmethyloxycarbonyl radical is removed with secondary amines.

Compounds of the general formula I, in which A or B represent an oxo-substituted or thioxo-substituted imidazolidine ring, can also be prepared by the reaction of amino acids, N-alkylamino acids or, preferably, their esters (for example methyl, ethyl, benzyl or tert-butyl esters) with an isocyanate or an isothiocyanate and subsequent heating of the resulting urea derivative or thiourea derivative with acid. Under these circumstances, hydrolysis of the ester function takes place at the same time.

For example, a compound of the general formula IV

 $R^1$-(A)$_a$-CH(NH$_2$)-COOCH$_3$  (IV)

can be reacted with a compound of the general formula V

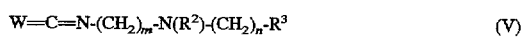 W=C=N-(CH$_2$)$_m$-N(R$^2$)-(CH$_2$)$_n$-R$^3$  (V)

in which A, a, $R^1$, $R^2$, $R^3$, m and n are defined as indicated above, and W denotes oxygen or sulphur, to give a compound of the general formula VI.

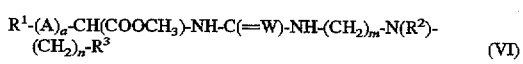 $R^1$-(A)$_a$-CH(COOCH$_3$)-NH-C(=W)-NH-(CH$_2$)$_m$-N(R$^2$)-(CH$_2$)$_n$-R$^3$  (VI)

The latter can be cyclized by heating with acid, with hydrolysis of the ester functions, to give a compound of the general formula Ia.

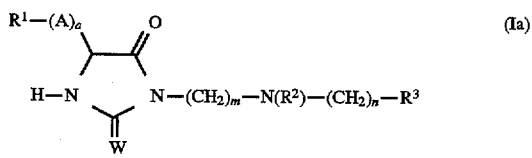

(Ia)

Alternatively, compounds of the general formula Ia can be obtained (in analogy with S. Goldschmidt, M. Wich, Liebigs Ann. Chem. 575 (1952) 217–231; C. Tropp, Chem. Ber. 61, (1928) 1431–1439) by reaction of compounds of the general formula VII

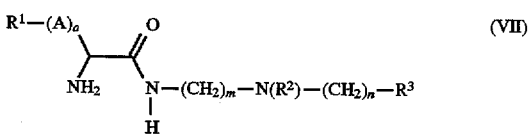

(VII)

with phosgene or thiophosgene, or corresponding equivalents, to give the esters of the imidazolidine derivatives and subsequent hydrolysis to give the carboxylic acids.

The guanylation of the amino function can be carried out with the following reagents:

1. O-Methylisourea (S. Weiss and H. Krommer, Chemiker Zeitung 98 (1974) 617–618),
2. S-Methylisothiourea (R. F. Borne, M. L. Forrester and I. W. Waters, J. Med. Chem. 20 (1977) 771–776),
3. Nitro-S-methylisothiourea (L. S. Hafner and R. E. Evans, J. Org. Chem. 24 (1959) 1157),
4. Formamidinosulphonic acid (K. Kim, Y.-T. Lin and H. S. Mosher, Tetrah. Lett. 29 (1988) 3183–3186),
5. 3,5-Dimethyl-1-pyrazolylformamidinium nitrate (F. L. Scott, D. G. O'Donovan and J. Reilly, J. Amer. Chem. Soc. 75 (1953) 4053–4054),
6. N,N'-Di-tert-butyloxycarbonyl-S-methylisothiourea (R. J. Bergeron and J. S. McManis, J. Org. Chem. 52 (1987) 1700–1703), 7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widding, P. Andrews, H.-P. Schulz and H. Thomas, Arzneim. Forsch./Drug Res. 34 (1984) 531–542).

Formamidines can be prepared from the corresponding cyano compounds by the addition of alcohols (e.g. methanol or ethanol) in acidic anhydrous medium (e.g. dioxane, methanol or ethanol) and subsequent treatment with ammonia in alcohols (e.g. isopropanol, methanol or ethanol) (G. Wagner, P. Richter and Ch. Garbe, Pharmazie 29 (1974) 12–15). A further method of preparing formamidines is the addition of $H_2S$ to the cyano group, followed by methylation of the resulting thioamide and subsequent reaction with ammonia (East German (DDR) Patent No. 235 866).

The compounds of the general formula I and their physiologically tolerated salts can be administered as medicines on their own, in mixtures with each other, or in the form of pharmaceutical preparations which permit enteral or parenteral use and which contain, as the active constituent, an effective dose of at least one compound of the general formula I, or a salt thereof, in addition to customary pharmaceutically harmless excipients and additives. The preparations normally contain about 0.5 to 90% by weight of the therapeutically active compound.

The medicines can be administered orally. e.g. in the form of pills, tablets, lacquered tablets, coated tablets, granules, hard and soft gelatine capsules, solutions, syrups, emulsions or suspensions, or aerosol mixtures. However, administration can also take place rectally, e.g. in the form of suppositories, or parenterally, e.g. in the form of solutions for injection, microcapsules or rods, percutaneously, e.g. in the form of ointments or tinctures, or nasally, e.g. in the form of nasal sprays.

The pharmaceutical preparations are produced in a manner known per se, with pharmaceutically inert inorganic or organic excipients being used. For example, lactose, corn starch or derivatives thereof, talc, stearic acid or its salts, etc., can be used for preparing pills, tablets, coated tablets and hard gelatine capsules. Excipients for soft gelatine capsules and suppositories are, e.g., fats, waxes, semi-solid and liquid polyols, natural or hardened oils, etc. Suitable excipients for preparing solutions and syrups are, e.g., water, sucrose, invert sugar, glucose, polyols, etc. Suitable excipients for preparing solutions for injection are water, alcohols, glycerol, polyols, vegetable oils, etc. Suitable excipients for microcapsules, implants or rods are mixed polymers of glycolic acid and lactic acid.

In addition to the active substances and excipients, the pharmaceutical preparations can also contain additives, such as, for example, fillers, extenders, disintegrants, binding agents, glidants, wetting agents, stabilizers, emulsifiers, preservatives, sweeteners, colorants, flavorants or aromatizing agents, thickeners, diluents or buffering substances, and, in addition, solvents or solubilizing agents, or agents for achieving a depot effect, as well as salts for altering the osmotic pressure, coating agents or antioxidants. They can also contain two or more compounds of the general formula I, or their physiologically tolerated salts, and one or more different therapeutically active compounds in addition.

Different therapeutically active substances of this type are, for example, agents promoting blood circulation, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronary dilators, such as carbocromen; dipyridamole, nifedipine and perhexiline; antianginal compounds, such as isosorbide dinitrate, isosorbide mononitrate, glycerol nitrate, molsidomine and verapamil; β-blockers, such as propranolol, oxprenolol, atenolol, metoprolol and penbutolol. In addition to this the compounds can be combined with other substances which stimulate cognition, such as, for example, piracetam, or with substances with CNS activity, such as pirlindole, sulpiride, etc.

The dose may be varied within wide limits and is to be adjusted to the individual circumstances in each separate case. In general, a daily dose of about 0.1 to 1 mg/kg, preferably 0.3 to 0.5 mg/kg, of body weight is appropriate for obtaining effective results in the case of oral administration, while in the case of intravenous administration the daily dose is in general about 0.01 to 0.3 mg/kg, preferably 0.05 to 0.1 mg/kg, of body weight. Normally, and in particular when larger quantities are being administered, the daily dose is divided up into several, e.g. 2, 3 or 4, parts which are then administered separately. Where appropriate, it may be necessary, depending on the individual response, to deviate from the daily dose indicated, either upwards or downwards. Per dose, pharmaceutical preparations normally contain 0.2 to 50 mg, preferably 0.5 to 10 mg, of active compound of the general formula I, or of its physiologically tolerated salts.

The compounds of the formula I according to the invention are able to inhibit cell-cell adhesion which is based on the interaction of Arg-Gly-Asp-containing proteins, such as fibronectin, fibrinogen or the von Willebrand factor, with the so-called integrins. Integrins are transmembrane glycoproteins, receptors for Arg-Gly-Asp-containing cell matrix glycoproteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). In addition, they inhibit the binding of other adhesive proteins, such as vitronectin, collagen and laminin, to the corresponding receptors on the surface of various cell types.

The compounds of the general formula I according to the invention inhibit blood-platelet aggregation, the formation of metastases by carcinoma cells and the binding of osteoclasts to bone surfaces.

The compounds of the general formula I can be used acutely when there is danger of thrombosis and chronically in the prevention of arteriosclerosis and thrombosis, e.g. in the therapy and prophylaxis of arterial vascular disorders, as in acute myocardial infarction, secondary prevention of myocardial infarction, reocclusion prophylaxis following lysis and dilatation (PTCA), unstable angina pectoris, transitory ischaemic attacks, stroke, coronary bypass operations, including reocclusion prophylaxis in association with bypass, pulmonary embolism, peripheral arterial occlusion disease and dissecting aneurysm; in the therapy of venous and microcirculatory vascular disorders, such as deep vein thrombosis, disseminated intravascular coagulation, postoperative and post-partum trauma, surgical or infectious shock and septicaemia, or in disorders involving hyperreactive thrombocytes, thrombotic thrombocytopenic purpura, pre-eclampsia, premenstrual syndrome, dialysis or extracorporeal circulation; the compounds may additionally be used during cancer operations and for cancer prophylaxis. In addition, osteoporosis can be prevented by inhibiting the binding of osteoclasts to the bone surface.

The compounds are tested, in particular, for their ability to inhibit blood-platelet aggregation and the adherence of fibrinogen to blood platelets (gel-filtered blood platelets from human donor blood are used which are activated with ADP or thrombin), as well as for their in-vivo ability to inhibit blood-platelet aggregation and thrombosis.

The test is of the ability of the compounds according to the invention to inhibit the binding of fibrinogen to its receptor (glycoprotein IIb/IIIa) on intact, gel-filtered human blood platelets. The value given is the Ki value for inhibition of the binding of $^{125}$I-fibrinogen following stimulation with ADP (10 µM). (Literature: J. S. Bennett and G. Vilaire, J. Clin. Invest. 64 (1979), 1393–1401; E. Kornecki et al., J. Biol. Chem. 256 (1981), 5695–5701; G. A. Marguerie et al., J. Biol. Chem. 254 (1979), 5357–5363; G. A. Marguerie et al., J. Biol. Chem. 255 (1980), 154–161).

In this test, the following result is obtained for the compound of Example 1 below:

| Example | Ki (µM), ADP-stimulated |
| --- | --- |
| 1 | 0.42 |

As a functional test, the ability is measured of the compounds according to the invention to inhibit the aggregation of gel-filtered human blood platelets following stimulation with ADP or thrombin. The value given is the $IC_{50}$ value of the inhibition. (Literature: G. A. Marguerie et al., J. Biol. Chem. 254 (1979), 5357–5363).

In this test, the following results were obtained for the compounds of Examples 1 and 2 immediately below:

| Example | ADP-stimulated $IC_{50}$ (µM) | Thrombin-stimulated $IC_{50}$ (µM) |
| --- | --- | --- |
| 1 | 1.5 | 1.0 |
| 2 | 20 | 20 |

EXAMPLES

The products were identified by way of their mass spectra and/or NMR spectra.

Example 1

(1-(3-(3-(4-(Aminoiminomethyl)phenyl)acryloylamino) propyl)-3-(hydroxycarbonylphenylmethyl)ureido)acetic acid acetate
1a:
(1-(3-tert-Butoxycarbonylaminopropyl)-3-(methoxycarbonylphenylmethyl)ureido)acetic acid 2.8 g (12 mmol) of (3-tert-butoxycarbonylaminopropyl) glycine and 1.4 g (12 mmol) of N-ethylmorpholine are dissolved in 300 ml of dimethylformamide. 2.3 g (12 mmol) of methyl α-isocyanatophenylacetate are added dropwise at 100° C. The mixture is stirred at 100° C. for 1 h, allowed to cool down to room temperature, concentrated and chromatographed on silica gel using ethyl acetate/methanol 8:2.
Yield 2.4 g
1b:
(1-(3-Aminopropyl)-3-(methoxycarbonylphenylmethyl) ureido)acetic acid trifluoroacetate 2.3 g (5.4 mmol) of (1-(3-tert-butoxycarbonylaminopropyl)-3-(methoxycarbonylphenylmethyl)ureido)acetic acid are stirred at room temperature for 2 h together with 20 ml of 90% strength aqueous trifluoroacetic acid. After concentrating, the mixture is freeze dried.
Yield: 2.3 g
1c:
Methyl (3-(3-aminopropyl)-2,5-dioxoimidazolidin-1-yl) phenylacetate hydrochloride 2.9 g (9 mmol) of (1-(3-aminopropyl)-3-(methoxycarbonylphenylmethyl)ureido)acetic acid trifluoroacetate are dissolved in 50 ml of methanol. After cooling down to 0° C., 1.34 g (11 mmol) of thionyl chloride are slowly added dropwise. The mixture is allowed to warm up to room temperature, then stirred overnight, concentrated and crystallized by adding ethyl acetate and methanol.
Yield: 1.99 g Melting point: 90° C. DCI-MS: 306 (M+H$^+$)
1d:
Methyl (3-(3-(3-(4-aminoiminomethyl)phenyl) acryloylamino)propyl)-2,5-dioxoimidazolidin-1-yl) phenylacetate 1 g (2.93 mmol) of methyl (3-(3-aminopropyl)-2,5-dioxoimidazolidin-1-yl)phenylacetate hydrochloride is dissolved in 20 ml of dimethylformamide. Following the addition of 0.74 g (3 mmol) of 4-amidinocinnamoyl chloride hydrochloride and N-ethylmorpholine, the mixture is stirred at room temperature and concentrated, and the residue is then, for purification, chromatographed on Sephadex LH20 using an homogeneous mixture of butanol/glacial acetic acid/water.
Yield: 140 mg FAB-MS: 478 (M+H$^+$)
1e:
(1-(3-(3-(4-(Aminoiminomethyl)phenyl)acryloylamino) propyl)-3-(hydroxycarbonylphenylmethyl)ureido)acetic acid acetate 78 mg (0.165 mmol) of methyl (3-(3-(3-(4-(aminoiminomethyl)phenyl)acryloylamino)propyl)-2,5-dioxoimidazolidin-1-yl)phenylacetate are stirred at room temperature for 20 h together with 2 ml of 1N sodium hydroxide solution, 5 ml of water and 5 ml of methanol. Following concentration, the residue is, for purification, chromatographed on Sephadex LH20 using an homogeneous mixture of butanol/glacial acetic acid/water.
Yield: 23 mg Melting point: 240° C. FAB-MS: 482 (M+H$^+$).

Example 2

(2-(4-(4-(Aminoiminomethyl)benzyl)-2,5-dioxoimidazolidin-1-yl)ethyl)-(9-fluorenylmethoxycarbonyl)aminoacetic acid
2a:
Methyl (2-isocyanatoethyl)-(9-fluorenylmethoxycarbonyl)-aminoacetate 5 g (12.8 mmol) of (2-aminoethyl)-(9-fluorenylmethoxycarbonyl)glycine methyl ester hydrochloride are suspended in 100 ml of anhydrous toluene. 6.3 g of phosgene are passed in at room temperature, and the mixture is then heated to 100° C. and further phosgene passed in at 100° C. within the space of 6 h. After adding triethylamine, the salt is separated off and the reaction mixture is concentrated and used directly for further reaction.
Yield: 4.5 g
2b:
Methyl (3-(4-(aminoiminomethyl)phenyl)-2-(3-(2-methoxycarbonylmethyl)-(9-fluorenylmethoxycarbonyl) amino)ethyl)ureido)propionate acetate 1.9 g (5 mmol) of methyl (2-isocyanatoethyl)-(9-fluorenylmethoxycarbonyl)aminoacetate in 20 ml of dimethylformamide are added dropwise, at 0° C., to 1.5 g (5 mmol) of 4-amidinophenylalanine methyl ester dihydrochloride and 2.5 ml (20 mmol) of N-ethylmorpholine in 20 ml of dimethylformamide. The mixture is stirred at room temperature for 12 h and at 50° C. for 1 h, and potassium hydrogen sulphate solution is then added and the mixture extracted with ethyl acetate; the organic phase is dried, concentrated and chromatographed, for purification, on Sephadex LH20 using an homogeneous mixture of butanol/ glacial acetic acid/water.

Yield: 1.4 g

2c:
(2-(4-(4-(Aminoiminomethyl)benzyl)-2,5-dioxoimidazolidin-1-yl)ethyl)-(9-fluorenylmethoxycarbonyl)aminoacetic acid hydrochloride 1.2 g (1.88 mmol) of (2-(4-(4-(aminoiminomethyl)benzyl)-2,5-dioxoimidazolidin-1-yl)ethyl)-(9-fluorenylmethoxycarbonyl)aminoacetic acid are heated at 90° C. for 20 minutes together with 24 ml of 10% strength hydrochloric acid and 24 ml of acetic acid. Following concentration, chromatography takes place, for purification, on Sephadex LH20 using methanol.

Yield: 890 mg FAB-MS: 556 (M+H$^+$)

Example 3

(1-(2-(4-(4-(Aminoiminomethyl)benzyl)-2,5-dioxoimidazolidin-1-yl)ethyl)-3-(methoxycarbonylphenylmethyl)ureido)acetic acid 3a:
(2-(4-(4-(Aminoiminomethyl)benzyl)-2,5-dioxoimidazolidin-1-yl)ethyl)aminoacetic acid 880 mg (1.49 mmol) of (2-(4-(4-(aminoiminomethyl)benzyl)-2,5-dioxoimidazolidin-1-yl)ethyl)-(9-fluorenylmethoxycarbonyl)aminoacetic acid hydrochloride are dissolved in 50 ml of dimethylformamide. Following the addition of 15 ml of piperidine, the mixture is stirred at room temperature for 5 hours and then concentrated, after which water is added to the residue, which is then extracted with methylene chloride. The water phase is acidified to pH 2, concentrated and chromatographed, for purification, on Sephadex LH20 using an homogeneous mixture of butanol/ glacial acetic acid/water.

Yield: 285 mg FAB-MS: 334 (M+H$^+$)

3b:
(1-(2-(4-(4-(Aminoiminomethyl)benzyl)-2,5-dioxoimidazolidin-1-yl)ethyl)-3-(methoxycarbonylphenylmethyl)ureido)acetic acid 60 mg (0.3 mmol) of isocyanatophenylglycine methyl ester in 5 ml of dimethylformamide are added dropwise, at 0° C., to 100 mg (0.3 mmol) of (2-(4-(4-(aminoiminomethyl)benzyl)-2,5-dioxoimidazolidin-1-yl)ethyl)aminoacetic acid and 35 mg (0.3 mmol) of N-ethylmorpholine in 10 ml of dimethylformamide. The mixture is stirred at room temperature for 12 h, concentrated and then chromatographed, for purification, on Sephadex LH20 using an homogeneous mixture of butanol/glacial acetic acid/water.

Yield: 71 mg FAB-MS: 525 (M+H$^+$)

Example 4

Methyl N-(2-(3-(4-(aminoiminomethyl)phenyl)acryloylamino)ethyl)-N-(9-fluorenylmethoxycarbonyl)aminoacetate hydrochloride 4a:
N-(2-tert-Butoxycarbonylaminoethyl)-N-(9-fluorenylmethoxycarbonyl)aminoacetic acid 10.9 g (50 mmol) of N-(2-tert-butoxycarbonylaminoethyl)aminoacetic acid are stirred together with 50 ml of water, 11.3 g (135 mmol) of sodium hydrogen carbonate and 50 ml of tetrahydrofuran. Subsequently, 24.3 g (72 mmol) of N-(9-fluorenylmethoxycarbonyloxy)succinimide are added. The mixture is stirred at room tmeperature for 20 h and the salt removed by filtration; the filtrate is acidified and the phases separated, and the organic phase is then concentrated.

Yield: 21.0 g (99%)

4b:
N-(2-Aminoethyl)-N-(fluorenylmethoxycarbonyl)aminoacetic acid hydrochloride 80 ml of 90% strength trifluoroacetic acid are added to 21.0 g (48 mmol) of N-(2-tert-butoxycarbonylaminoethyl)-N-(fluorenylmethoxycarbonyl)aminoacetic acid. The mixture is stirred at room temperature for 3 h and then concentrated under high vacuum. The residue is dissolved in ethyl acetate and ethereal hydrochloric acid is then added and the hydrochloride which crystallizes out is filtered off with suction and dried.

Yield: 13.1 g (71%) Melting point: 200°–205° C.

4c:
Methyl N-(2-aminoethyl)-N-(9-fluorenylmethoxycarbonyl)aminoacetate hydrochloride 2.15 ml of thionyl chloride are added dropwise, at 0° C., to 75 ml of anhydrous methanol. Subsequently, 7.5 g (20 mmol) of N-(2-aminoethyl)-N-(9-fluorenylmethoxycarbonyl)aminoacetic acid hydrochloride are added in portions. The mixture is stirred at 0° C. for one hour, allowed to warm to room temperature, and then stirred further overnight. The reaction solution is concentrated and the precipitate is filtered off with suction and dried.

Yield: 6.4 g (82%) Melting point: 279°–282° C. DCI-MS: 355 (M+H$^+$)

4d:
Methyl N-(2-(3-(4-(aminoiminomethyl)phenyl)acryloylamino)ethyl)-N-(9-fluorenylmethoxycarbonyl)aminoacetate hydrochloride 0.7 g (6 mmol) of N-ethylmorpholine and 0.8 g (4 mmol) of DCC are added, at 0° C., to 0.7 g (3 mmol) of 4-amidinocinnamic acid hydrochloride, 1.2 g (3 mmol) of methyl N-(2-aminoethyl)-N-(9-fluorenylmethoxycarbonyl) aminoacetate hydrochloride and 0.4 g (3 mmol) of hydroxybenzotriazole in 20 ml of dimethylformamide. The mixture is stirred at 0° C. for one hour and then at room temperature for 20 h, filtered from the precipitated urea and concentrated. The residue is taken up in ethyl acetate and washed with sodium hydrogen carbonate solution, and the organic phase is dried and concentrated. The product is chromatographed, for purification, on Sephadex LH20 using an homogeneous mixture of butanol/glacial acetic acid/water.

Yield: 340 mg (20%) FAB-MS: 563.3 (M+H$^+$)

Example 5

(1-(2-(3-(4-(Aminoiminomethyl)phenyl)acryloylamino)ethyl)-3-hydroxycarbonylphenylmethyl)ureido)acetic acid 5a:
Methyl 4-tert-butoxycarbonylamidinocinnamate 0.86 g (8 mmol) of sodium carbonate in 20 ml of water is added, at room temperature, to 1.95 g (8.1 mmol) of methyl 4-amidinocinnamate hydrochloride and 3.5 g (16.2 mmol) of di-tert-butyl dicarbonate in 40 ml of methylene chloride. The precipitate dissolves following vigorous stirring. The organic phase is separated off, concentrated and crystallized using ether.

Yield: 1.79 g (73%)

5b:
4-tert-Butoxycarbonylimidinocinnamic acid sodium salt 730 mg (2.4 mmol) of methyl 4-tert-butoxycarbonylamidinocinnamate are dissolved in 50 ml of methanol. The pH is adjusted to 10 by adding 1N sodium hydroxide solution and the mixture is stirred until the reaction is complete. The solution is concentrated and freeze dried.

Yield: 748 mg

5c:

Methyl (3-(2-(3-(4-(aminoiminomethyl)phenyl) acryloylamino)ethyl)-2,5-dioxoimidazolidin-1-yl) phenylacetate hydrochloride 730 mg (2.34 mmol) of 4-tert-butoxycarbonylamidinocinnamic acid sodium salt are dissolved in 50 ml of dimethylformamide and 531 mg (2.57 mmol) of DCC and 316 mg (2.34 mmol) of HOBt are then added at 0° C. The mixture is stirred for 50 minutes and 355 mg (2.34 mmol) of methyl (3-(2-aminoethyl)-2,5-dioxoimidazolidin-1-yl)phenylacetate hydrochloride are then added. After stirring at room temperature for 20 h, the mixture is concentrated and the residue is chromatographed, for purification, on silica gel using a mixture of methylene chloride, methanol, glacial acetic acid and water=85:15:2:2. The fractions containing the pure substance are concentrated and freeze dried.

Yield: 520 mg

5d:

1-(2-(3-(4-(Aminoiminomethyl)phenyl)acryloylamino) ethyl)-3-(hydroxycarbonylphenylmethyl)ureido)acetic acid 500 mg (1 mmol) of methyl (3-(2-(3-(4-(aminoiminomethyl)phenyl)acryloylamino)ethyl)-2,5-dioxoimidazolidin-1-yl)phenylacetate hydrochloride are dissolved in 10 ml of methanol and 10 ml of water and 5 ml of 1N sodium hydroxide solution are then added. The mixture is stirred at room temperature overnight, concentrated and chromatographed, for purification, on Sephadex LH20 using an homogeneous mixture of butanol/glacial acetic acid/water.

Yield: 350 mg FAB-MS: 468.3 (M+H$^+$)

Example 6

(3-(Carboxyphenylmethyl)-1-(2-(2-(4-guanidinophenyl) acetylamino)ethyl)ureido)acetic acid 6a:

Methyl (3-(2-aminoethyl)-2,5-dioxoimidazolidin-1-yl) phenylacetate hydrochloride 0.9 ml (12 mmol) of thionyl chloride are added dropwise, at 0° C., to 4.1 g (10 mmol) of (1-(2-tertbutoxycarbonylaminoethyl)-3-(methoxycarbonylphenylmethyl)ureido)acetic acid in 50 ml of methanol. The mixture is allowed to warm to room temperature and then stirred further overnight, followed by filtering off with suction and drying.

Yield: 1.97 g (60%)

6b:

Methyl (3-(2-(2-(4-nitroguanidinophenyl)acetylamino) ethyl)-2,5-dioxoimidazolidin-1-yl)phenylacetate 270 mg (1.13 mmol) of 4-nitroguanidinophenylacetic acid are dissolved in 50 ml of dimethylformamide, and 270 mg (1.25 mmol) of DCC and 150 mg (1.13 mmol) of HOBt are then added at 0° C. The mixture is stirred for 30 minutes and 370 mg (1.13 mmol) of methyl (3-(2-aminoethyl)-2,5-dioxoimidazolidin-1-yl)phenylacetate hydrochloride and 150 μl (1.13 mmol) of N-ethylmorpholine are then added. After stirring at room temperature for 20 h, the mixture is concentrated and ethyl acetate and methanol are added to the residue and the insoluble dicyclohexylurea is filtered off with suction. The filtrate is concentrated and methylene chloride is then added, and the solution is washed with sodium hydrogen carbonate solution and potassium hydrogen sulphate solution, dried and concentrated.

Yield: 540 mg

6c:

(3-(Carboxyphenylmethyl)-1-(2-(2-(4-guanidinophenyl) acetylamino)ethyl)ureido)acetic acid 380 mg (0.74 mmol) of methyl (3-(2-(2-(4-nitroguanidinophenyl)acetylamino)ethyl)-2,5-dioxoimidazolidin-1-yl)phenylacetate are dissolved in 5 ml of methanol and 5 ml of water. After adding 1.5 ml (1.5 mmol) of 1N sodium hydroxide solution, the mixture is stirred at room temperature for 5 h, concentrated and freeze dried. The residue is dissolved in 40 ml of methanol and 40 ml of water; 50 mg of 10% palladium on carbon are then added to the solution, which is hydrogenated at room temperature. After concentrating, chromatography takes place, for purification, on Sephadex LH20 using an homogeneous mixture of butanol/glacial acetic acid/water.

Yield: 200 mg (57%) FAB-MS: 471.3 (M+H$^+$)

Example 7

(3-(Carboxyphenylmethyl)-1-(3-(4-guanidinobenzoylamino)propyl)ureido)acetic acid 7a:

Methyl (3-(3-(4-guanidinobenzoylamino)propyl)-2,5-dioxoimidazolidin-1-yl)phenylacetate hydrochloride 384 mg (1.14 mmol) of 4-nitrophenyl 4-guanidinobenzoate, 390 mg (1.14 mmol) of methyl (3-(3-aminopropyl)-2,5-dioxoimidazolidin-1-yl)phenylacetate hydrochloride, 55 mg (0.4 mmol) of HOBt and 140 mg (1.2 mmol) of N-ethylmorpholine are stirred at room temperature for 5 h in 10 ml of dimethylformamide. Following concentration, chromatography takes place, for purification, on silica gel using a mixture of methylene chloride, methanol, glacial acetic acid and water=85:15:2:2. The fractions containing the pure substance are concentrated and freeze dried.

Yield: 385 mg (67%)

7b:

(3-(Carboxyphenylmethyl)-1-(3-(4-guanidinobenzoylamino)propyl)ureido)acetic acid 380 mg (0.76 mg) of methyl (3-(3-(4-guanidinobenzoylamino)propyl)-2,5-dioxoimidazolidin-1-yl)phenylacetate hydrochloride are dissolved in 10 ml of methanol and 10 ml of water, and 2.28 ml of 1N sodium hydroxide solution are then added. The mixture is stirred at room temperature overnight, concentrated and chromatographed, for purification, on Sephadex LH20 using an homogeneous mixture of butanol/glacial acetic acid/water.

Yield: 276 mg (77%) FAB-MS: 471.4 (M+H$^+$)

Example 8

N-(2-(4-(4-Benzyloxycarbonylguanidinophenyl)-2,5-dioxoimidazolidin-1-yl)ethyl)-N-(9-fluorenylmethoxycarbonyl)amino acetic acid Example 9

N-(2-((4-trans-Aminomethylcyclohexylcarbonyl) aminoacetylamino)ethyl)-N-((D)-1,2,3,4-tetrahydroisoquinolin-3-ylcarbonyl)aminoacetic acid Example 10

N-(2-((4-trans-Aminomethylcyclohexylcarbonyl) aminoacetylamino)ethyl)-N-(phenylalaninyl)aminoacetic acid Example 11

N-(2-((4-trans-Aminomethylcyclohexylcarbonyl) aminoacetylamino)ethyl)-N-(phenylacetyl)aminoacetic acid Example 12

N-(2-((4-Aminomethylbenzoyl)aminoacetylamino)ethyl)-N-(phenylacetyl)aminoacetic acid

Example 13

N-(2-((4-Aminomethylbenzoyl)aminoacetylamino)ethyl)-N-(3-phenylpropionyl)aminoacetic acid

Example 14

N-(2-((4-Aminomethylbenzoyl)aminoacetylamino)ethyl)-N-(acetylphenylalaninyl)aminoacetic acid

We claim:

1. Compounds of the general formula I

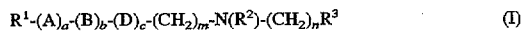

in which A denotes a divalent radical from the group consisting of methylene, ethylene, trimethylene, tetramethylene, cyclohexylene, phenylene, phenylenemethyl, phenyleneethenyl, and phenylenemethylene;

B denotes a divalent radical from the group consisting of methylene, ethylene, trimethylene, tetramethylene, vinylene, phenylene, 2,5-dioxoimidazolidine-1,4-diyl, 5-oxo-2-thioxoimidazolidine-1,4-2,5-dioxopyrrolidine-1,4-diyl and 2,4-dioxooxazolidine-3,5-diyl;

D denotes a divalent radical from the group consisting of carbonylimino, iminocarbonyl and iminocarbonylimino;

$R^1$ denotes —$CH_2$-NH-X, —C(=NH)-NH-$X^1$ or —NH-C(=$NX^1$)-NH-$X^1$; X and $X^1$ denote hydrogen, ($C_1$–$C_6$)-alkylcarbonyl, ($C_1$–$C_6$)-alkoxycarbonyl or ($C_1$–$C_8$)-alkylcarbonyloxy-($C_1$–$C_6$)-alkoxycarbonyl;

$R^2$ denotes —$COR^4$, —$COOR^4$, —CO-NH-$R^4$ or —CS-NH-$R^4$;

$R^3$ denotes —COOH or —COO-($C_1$–$C_{18}$)-alkyl;

$R^4$ denotes ($C_1$–$C_6$)-alkyl or ($C_6$–$C_{14}$)-aryl-($C_1$–$C_8$)-alkyl, or, in the case where $R^2$ represents —CO-NH-$R^4$ or —CSNH-$R^4$, —NH-$R^4$ represents an α-amino acid residue or its ω-amino-($C_2$–$C_8$)-alkyl amide;

a,b and c denote 0 or 1, but cannot all simultaneously be 0; and m represents 2 or 3 and n represents 1, as well as physiologically tolerated salts thereof.

2. Compounds according to claim 1, characterized in that α-amino acid residues representing —NH-$R^4$ are the valine, lysine, phenylalanine, phenylglycine or tryptophan residues.

3. Compounds according to claim 1, characterized in that the ω-amino-($C_2$–$C_8$)-alkyl amide is the 4-aminobutyl amide.

4. Process for preparing compounds of the general formula I of claim 1, characterized in that a fragment condensation of a compound of the general formula II

with a compound of the general formula III

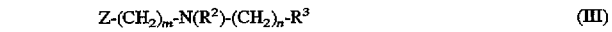

is carried out, where the radicals A, B, $R^1$, $R^2$ and $R^3$, as well as a, b, m and n, are defined as indicated in claim 1, and Y represents hydroxycarbonyl, alkoxycarbonyl or an activated carboxylic acid derivative, and Z represents amino or in which Y represents amino, and Z represents hydroxycarbonyl, alkoxycarbonyl or an activated carboxylic acid derivative.

5. Pharmaceutical preparation, characterized in that it contains one or more compounds of the general formula I of claim 1, or a physiologically tolerated salt thereof, as the active compound, together with pharmaceutically acceptable excipients and additives and, where appropriate, one or more different pharmacological active compounds in addition.

6. Process for preparing a pharmaceutical preparation containing one or more compounds of the general formula I of claim 1, or a physiologically tolerated salt thereof, characterized by mixing such compounds, together with pharmaceutically acceptable excipients and additives and, where appropriate, one or more different pharmacological active compounds in addition, into a suitable form for administration.

7. Method for inhibiting blood platelet aggregation, the formation of metastases by carcinoma cells and the binding of osteoctasts to bone surfaces which comprises administering to a host in need thereof an effective amount of a compound of the formula I of claim 1.

* * * * *